United States Patent
Chen et al.

(10) Patent No.: US 8,244,020 B2
(45) Date of Patent: Aug. 14, 2012

(54) METHOD AND SYSTEM FOR INTELLIGENT DIGITAL SUBTRACTION

(75) Inventors: Yunqiang Chen, Plainsboro, NJ (US); Tong Fang, Morganville, NJ (US); Sandra Martin, Herzogenaurauch (DE); Stefan Boehm, Oberasbach (DE); Peter Durlak, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 985 days.

(21) Appl. No.: 12/286,992

(22) Filed: Oct. 3, 2008

(65) Prior Publication Data

US 2009/0103682 A1 Apr. 23, 2009

Related U.S. Application Data

(60) Provisional application No. 60/980,860, filed on Oct. 18, 2007.

(51) Int. Cl.
*G06K 9/40* (2006.01)
*G06K 9/60* (2006.01)
*G06T 5/50* (2006.01)
*G01N 23/083* (2006.01)

(52) U.S. Cl. ...... 382/132; 382/128; 382/266; 378/98.12

(58) Field of Classification Search .................. 382/128, 382/130–132, 209, 217–220, 278, 325; 378/62, 378/65, 91, 98, 98.8, 98.11, 98.12, 210, 901
See application file for complete search history.

(56) References Cited

U.S. PATENT DOCUMENTS

| | | | |
|---|---|---|---|
| 5,345,938 A | 9/1994 | Nishiki et al. | |
| 7,218,702 B2 | 5/2007 | Mistretta et al. | |
| 7,233,689 B2 * | 6/2007 | Haupert et al. | 382/130 |
| 2007/0016015 A1 | 1/2007 | Camus et al. | |
| 2007/0183637 A1 * | 8/2007 | Kreuzer et al. | 382/128 |
| 2007/0276216 A1 | 11/2007 | Beyar et al. | |
| 2008/0021297 A1 | 1/2008 | Boosten | |
| 2008/0137935 A1 | 6/2008 | Spahn | |

* cited by examiner

*Primary Examiner* — Anastasia Midkiff

(57) ABSTRACT

A method and system for intelligent digital subtraction is disclosed. The method and system for intelligent digital subtraction can be used in a roadmap application for a coronary intervention. A mask image is obtained with vessels highlighted by contrast media. A guide wire is inserted into the vessels, and a guide wire image is obtained. A direct subtraction image is generated from the guide wire image and the mask image. A reduced noise subtraction image is generated based on mutual image information between the subtraction image and the guide wire image and mutual image information between the subtraction image and the mask image.

24 Claims, 4 Drawing Sheets

US 8,244,020 B2

METHOD AND SYSTEM FOR INTELLIGENT DIGITAL SUBTRACTION

This application claims the benefit of U.S. Provisional Application No. 60/980,860, filed Oct. 18, 2007, the disclosure of which is herein incorporated by reference.

BACKGROUND OF THE INVENTION

The present invention relates to x-ray imaging, and more particularly, to digital subtraction for an x-ray imaging roadmap application.

Digital subtraction is a common procedure for many medical imaging applications. For example, digital subtraction of x-ray images is commonly used for a roadmap application in coronary intervention or angioplasty procedures. In such a roadmap application, since vessels cannot be seen clearly in traditional x-ray images, a contrast media is injected into the vessels to highlight the vessels. This results in a mask image with the vessels highlighted. The contrast media is then flushed away, and during the intervention procedure, a guide wire is inserted into the vessels. To highlight the guide wire's location within the vessels, the mask image is subtracted from the current image that shows the presence of the guide wire. The final subtraction result ($I_{sub}$) is an image of the guidewire overlaid with the vessels to act as a roadmap to help a physician position the guidewire.

However, since the imaging noise in the mask image and imaging noise in the current image are independent of each other, the noise in the subtraction result is greater than in either of the two input images (i.e., mask image and current image). Accordingly, the signal to noise ratio of both of input images is better than that of the subtraction result. Thus, an improved subtraction procedure for roadmap applications that achieves a subtraction result with a better signal to noise ratio is desirable.

BRIEF SUMMARY OF THE INVENTION

The present invention provides a method and system for intelligent digital subtraction. Embodiments of the present invention utilize mutual image information between a mask image and a subtraction result and mutual image information between a guidewire image and a subtraction result to generate a reduced noise subtraction image. Embodiments of the present invention can be used to implement a roadmap application, for example, in a coronary intervention procedure.

In one embodiment of the present invention, a mask image is obtained with vessels highlighted by contrast media. A guide wire is inserted into the vessels, and a guide wire image is obtained. A direct subtraction image is generated from the guide wire image and the mask image. A reduced noise subtraction image is generated based on mutual image information between the subtraction image and the guide wire image and mutual image information between the subtraction image and the mask image.

These and other advantages of the invention will be apparent to those of ordinary skill in the art by reference to the following detailed description and the accompanying drawings.

DETAILED DESCRIPTION

The present invention relates to a method and system for intelligent digital subtraction of medical images. Embodiments of the present invention are described herein to give a visual understanding of the intelligent digital subtraction method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
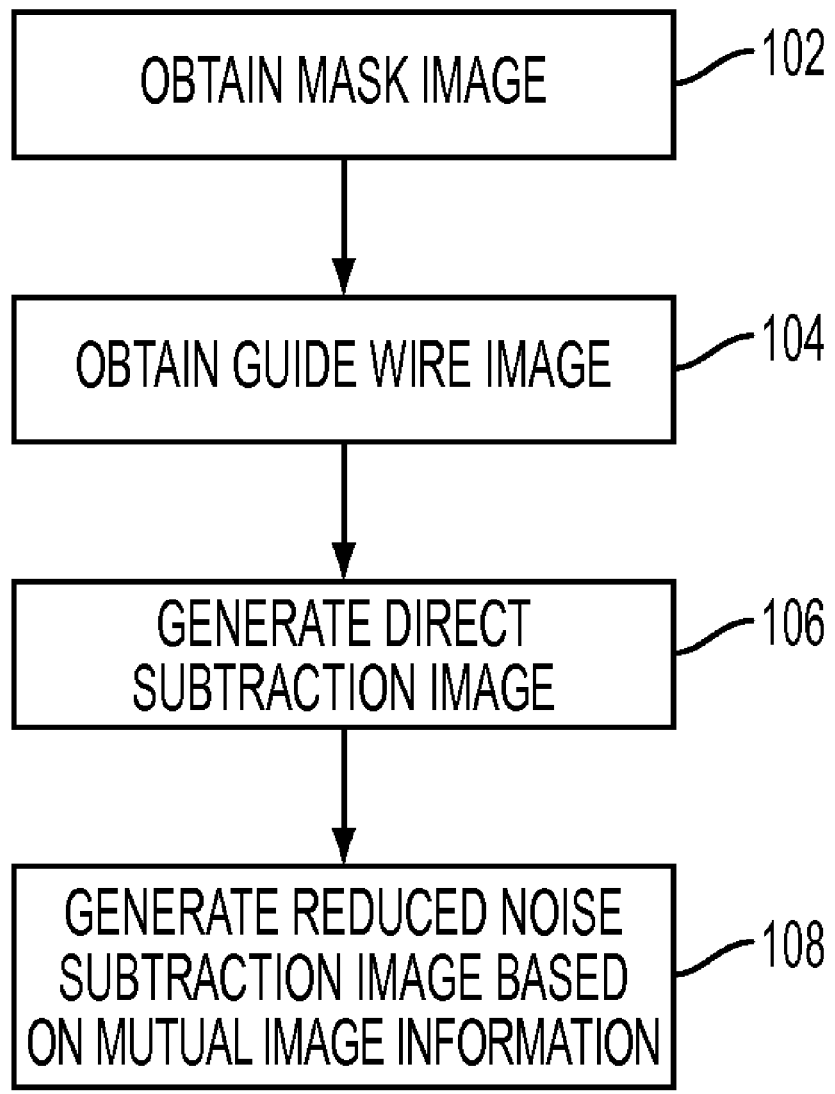
FIG. 1 illustrates a method for intelligent digital subtraction according to an embodiment of the present invention.
Figure 2:
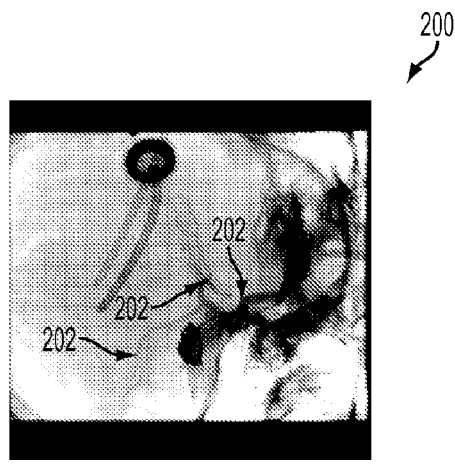
FIG. 2 illustrates an exemplary mask image.

FIG. 1 illustrates a method for intelligent digital subtraction according to an embodiment of the present invention. The method of FIG. 1 can be used for a roadmap application, for example in a coronary intervention procedure. As illustrated in FIG. 1, at step 102, a mask image is obtained. The mask image is an x-ray image in which vessels are highlighted. The mask image can be obtained from a sequence of x-ray images acquired with contrast media in vessels. Since vessels usually cannot be seen clearly in traditional x-ray images, injection of contrast media is used to highlight the vessels. Vessel related intervention procedures can be divided into different phases. In a first phase, contrast media is injected to highlight the vessels, and then flushed away. Vessels with the contrast media become darker than the surrounding soft tissue. Hence, the mask image can be obtained by taking the minimum of each pixel for all the image frames in a sequence of x-ray images acquired during this phase. It is also possible that the mask image can be obtained by loading a previously generated mask image from a computer readable medium, or memory or storage of a computer system. FIG. 2 illustrates an exemplary mask image. As illustrated in FIG. 2, image 200 is a mask image that shows vessels 202 that are highlighted with a contrast medium.

Figure 3:
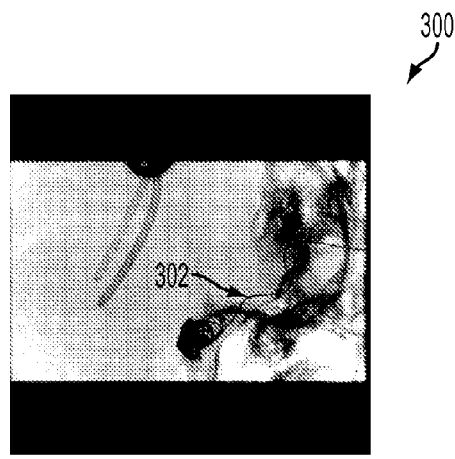
FIG. 3 illustrates an exemplary guide wire image.

Returning to FIG. 1, at step 104, a guide wire image is obtained. The guide wire image is an x-ray image that shows a guide wire that is inserted into the vessels, but the vessels are not highlighted with contrast media. During an intervention procedure, a guide wire is inserted into the vessels. However, since the contrast media has been flushed away, the vessels are almost invisible. The guide wire image can be obtained by receiving an x-ray image directly from an x-ray imaging device. FIG. 3 illustrates an exemplary guide wire image. As illustrated in FIG. 3, image 300 is a guide wire image in which a guide wire 302 can be seen.

Returning to FIG. 1, at step 106, a direct subtraction image is generated from the guide wire image and the mask image. In order to generate the direct subtraction image, the mask image is subtracted from the guide wire image. This results in an image with the vessels overlaid with the moving guide wire. However, this direct subtraction enhances the noise and reduces the signal to noise ratio in the direct subtraction image.

Figure 4:
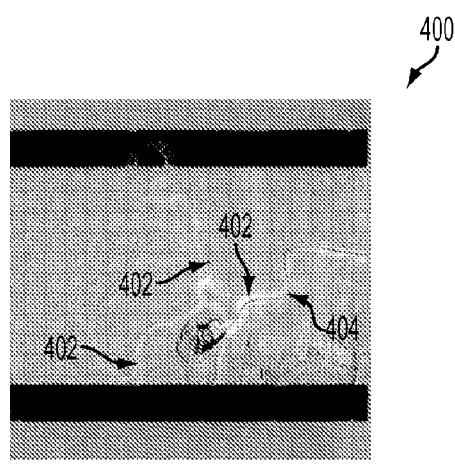
FIG. 4 illustrates an exemplary direct subtraction image.

FIG. 4 illustrates an exemplary direct subtraction image. As illustrated in FIG. 4, image 400 is a direct subtraction image resulting from subtracting the mask image 200 of FIG.

2 from the guide wire image 300 of FIG. 3. As shown in the direct subtraction image 400, the vessels 402 and the guide wire 404 can be seen.

According to an embodiment of the present invention, instead of using the direct subtraction image for the roadmap application, the direct subtraction image $I_{sub}(x, y)$ is used along with the mask image $M(x, y)$ and the guide wire image $I(x, y)$ to generate a reduced noise subtraction image. In order to maintain consistent contrast of an object (e.g., the guide wire) in the subtraction procedure, the images can be normalized before subtraction. In the formation of x-ray images, when an x-ray passes through the body tissues, it's energy is attenuated with the depth in the absorbing material according to a simple exponential function:

$$D = A \cdot \exp(-\alpha s),$$

where D is the energy received at the detector, $\alpha$ is the attenuation coefficient, A is the amount of energy transmitted, and s is the depth. When the x-ray hits the detector, its energy is measured and represented as an intensity value I, which reflects the attenuation through the whole path:

$$I = A \cdot \exp(-\int \alpha_s ds).$$

The attenuation coefficient $\alpha_s$ is different for different tissues. To obtain consistent contrast of the objects during the subtraction procedure, the mask and guide wire images are normalized by the log function before subtraction, such that:

$$I_{sub}(x,y) = \log(I(x,y)) - \log(M(x,y)).$$

Returning to FIG. 1, at step 108, a reduced noise subtraction image is generated from the mask image, guide wire image, and direct subtraction image based on mutual image information between the mask image and subtraction image and mutual image information between the guide wire image and the subtraction image. The reduced noise subtraction image can be generated by finding an optimal subtraction image in which image information that is mutual to the mask image or the guide wire image is preserved, and image information that is independent of the mask image and the guide wire image is removed.

The direct subtraction image $I_{sub}(x, y)$ has more noise (i.e., $N(x, y)$) that either of the input images (i.e., $\log(I(x, y))$ or $\log(M(x, y))$). If $I_{sub}^O(x, y)$ is the optimal subtraction result, which is noise free, then:

$$I_{sub}(x, y) = I_{sub}^O(x, y) + N(x, y),$$

where the noise $N(x, y)$ can be modeled as zero mean Gaussian noise.

Reducing the noise based only on $I_{sub}(x, y)$, can be attempted using a traditional Bayesian framework:

$$\hat{I}_{sub} = \underset{\hat{I}_{sub}}{\operatorname{argmax}} P(\hat{I}_{sub} | I_{sub}) = \underset{\hat{I}_{sub}}{\operatorname{argmax}} P_S(\hat{I}_{sub}) P_N(I_{sub} - \hat{I}_{sub}),$$

where $P_S( )$ and $P_N( )$ model the prior knowledge about the signal and noise, respectively. However, this traditional noise reduction technique relies solely on the prior models of the signal (e.g., smoothness), and noise (e.g., white Gaussian) to achieve noise reduction, and it is usually difficult to obtain accurate signal noise models. Furthermore, the noise is already amplified in the subtraction result, and this makes it even more difficult to detect and preserve the image signal.

In the intelligent digital subtraction method of FIG. 1, additional information is used to achieve better noise reduction. The optimal subtraction result contains image information that is similar to image information in either $\log(I(x, y))$ or $\log(M(x, y))$, while the information in the noise signal does not contain similar image information. Accordingly, mutual information terms for the guide wire image and the mask image can be added into the Bayesian framework to help discriminate the signal from the noise, instead of relying solely on prior models. Using the mutual information terms, an objective function for generating the reduced noise subtraction image $\hat{I}_{sub}$ can be defined as:

$$\hat{I}_{sub} = \underset{\hat{I}_{sub}}{\operatorname{argmin}} \left( -\log(P_N(I_{sub} - \hat{I}_{sub})) - MI(\hat{I}_{sub}, \log(I)) - MI(\hat{I}_{sub}, \log(M)) \right)$$

where $MI(\hat{I}_{sub}, \log(I))$ is a mutual image constraint that refers to image information that is mutual between the guide wire image and the reduced noise subtraction image, and $MI(\hat{I}_{sub}, \log(M))$ is a mutual image constraint that refers to image information that is mutual between the mask image and the reduced noise subtraction image. These mutual information constraints in the objective function enforce that the components that are independent with respect to the mask and guide wire images (i.e., $\log(M(x, y))$ and $\log(I(x, y))$ are removed from the reduced noise subtraction image. This provides more robust noise reduction than the traditional Bayesian framework.

Mutual information between images can be very expensive to calculate. In order to efficiently calculate the mutual information terms of the objective function, each mutual information term can be approximated based on the following property of independent random variables $N_1$ and $N_2$:

$$E(f(N_1)g(N_2)) = E(f(N_1)) \cdot E(g(N_2)).$$

Based on this property, mutual information can be approximated using a measure of independence, expressed as:

$$MI(N_1, N_2) = \sum_k \|E(f_k(N_1)g_k(N_2)) - E(f_k(N_1)) \cdot E(g_k(N_2))\|^2$$

where $f_k(N_1) = N_1^k$, $g_k(N_2) = N_2^k$.

In this approximation for MI, MI=0 if $N_1$ and $N_2$ are independent, and MI>0 if $N_1$ and $N_2$ are not independent (i.e., have mutual information). This approximation is used to calculate the mutual information terms, $MI(\hat{I}_{sub}, \log(I))$ and $MI(\hat{I}_{sub}, \log(M))$, in the objective function. Using these approximations for the mutual information terms in the objective function, the objective function is then solved to find the optimal solution. The objective function can be solved by taking the derivative of the objective function and setting it equal to zero. This results in a reduced noise subtraction image.

The reduced noise subtraction image can then be output. The reduced noise subtraction image can be output by displaying the reduced noise subtraction image, for example, on a display device of a computer system. The reduced noise subtraction image can also be output be storing the reduced noise subtraction image, for example, on a memory or storage of a computer system or a computer readable medium.

Figure 5:
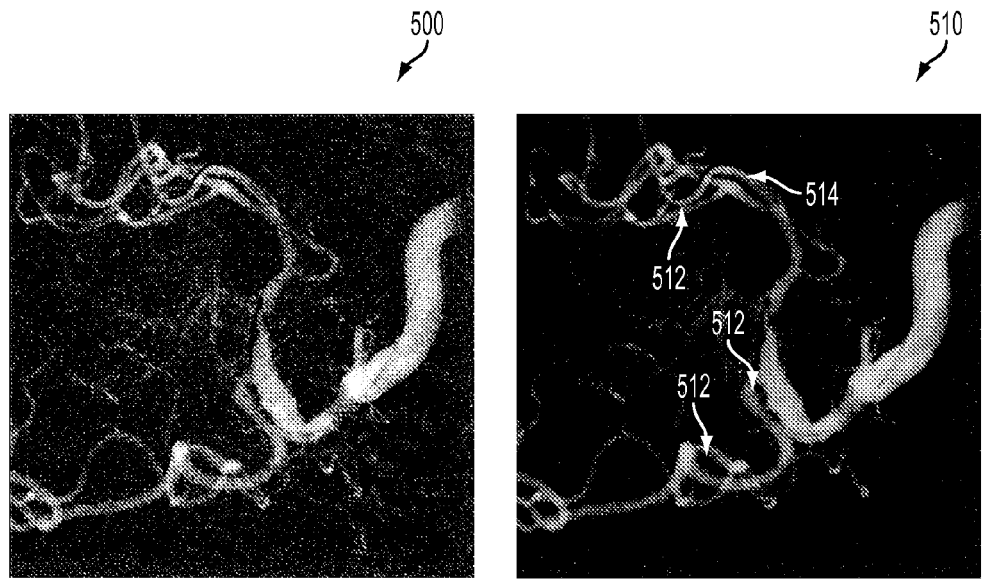
FIGS. 5 and 6 illustrate exemplary subtraction results generated using the intelligent digital subtraction method of FIG. 1.
Figure 6:
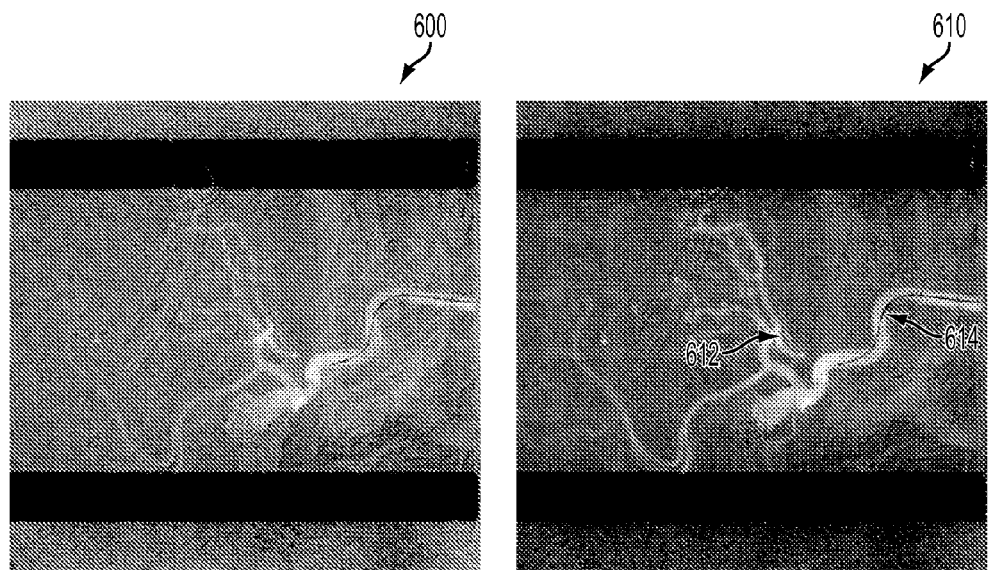

The reduced noise subtraction image that shows the vessels overlaid with the guide wire. FIGS. 5 and 6 illustrate exemplary subtraction results generated using the intelligent digital subtraction method of FIG. 1. As illustrated in FIG. 5, image 500 is a direct subtraction image, and image 510 is a reduced noise subtraction image generated using the intelligent digital subtraction method of FIG. 1. As shown in the reduced noise subtraction image 510, weak vessels 512 and the thin guide wire 514 are well perseverd in the reduced noise subtraction image 510, and noise is significantly reduced as compared to the direct subtraction image 500. As illustrated in FIG. 6, image 600 is a direct subtraction image and image 610 is a reduced noise subtraction image generated using the intelligent digital subtraction method of FIG. 1. As shown in the reduced noise subtraction image 610, the vessels 612 and the guide wire 614 are well perseverd, and noise is significantly reduced as compared to the direct subtraction image 600.

Figure 7:
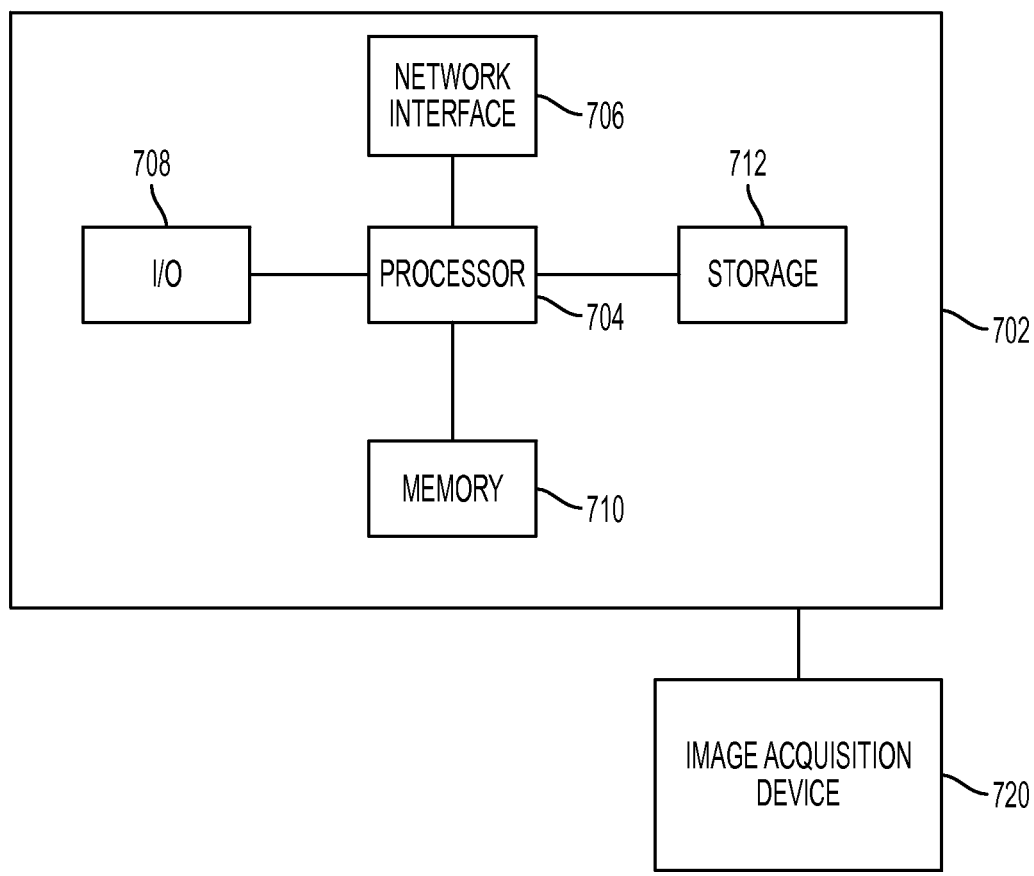
FIG. 7 is a high level block diagram of a computer capable of implementing the present invention.

The above-described methods for intelligent digital subtraction may be implemented on a computer using well-known computer processors, memory units, storage devices, computer software, and other components. A high level block diagram of such a computer is illustrated in FIG. 7. Computer 702 contains a processor 704 which controls the overall operation of the computer 702 by executing computer program instructions which define such operation. The computer program instructions may be stored in a storage device 712, or other computer readable medium, (e.g., magnetic disk) and loaded into memory 710 when execution of the computer program instructions is desired. Thus, all method steps described above for registering dual energy images, including the method steps illustrated in FIG. 1, may be defined by the computer program instructions stored in the memory 710 and/or storage 712 and controlled by the processor 704 executing the computer program instructions. An image acquisition device 720, such as an X-ray imaging device, can be connected to the computer 702 to input images to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.) One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for intelligent digital subtraction comprising:
   obtaining a mask image having highlighted vessels;
   obtaining a guide wire image of a guide wire inserted into a vessel;
   generating a direct subtraction image from the guide wire image and the mask image; and
   generating a reduced noise direct subtraction image based on mutual information between the direct subtraction image and the guide wire image and mutual image information between the mask image and the direct subtraction image.

2. The method of claim 1, wherein said step of obtaining a mask image comprises:
   acquiring a sequence of x-ray images with a contrast media injected into the vessels; and
   generating the mask image by determining the minimum intensity of each pixel in the sequence of x-ray images.

3. The method of claim 1, wherein said step of obtaining a guide wire image comprises:
   receiving an x-ray image of a guide wire inserted into the vessel without contrast media in the vessels.

4. The method of claim 1, wherein said step of generating a direct subtraction image comprises:
   normalizing the guide wire image and the mask image; and
   subtracting the normalized mask image from the normalized guide wire image.

5. The method of claim 4, wherein said step of normalizing the guide wire image and the mask image comprises:
   normalizing the guide wire image and the mask image with a logarithm function.

6. The method of claim 1, wherein said step of generating a reduced noise direct subtraction image comprises:
   reducing noise in the direct subtraction image by preserving image information in the direct subtraction image that is mutual to the mask image or the guide wire image, and removing image information in the direct subtraction image that is independent of the mask image and the guide wire image.

7. The method of claim 1, wherein said step of generating a reduced noise direct subtraction image comprises:
   solving an objective function having a first mutual information term for mutual image information between the guide wire image and the reduced noise direct subtraction image and a second mutual information term for mutual image information between the mask image and the reduced noise direct subtraction image.

8. The method of claim 7, wherein step of generating a reduced noise direct subtraction image comprises:
   approximating the first mutual information term of the objective function using a measure of independence between the reduced noise subtraction image and the guide wire image, and approximating the second mutual information term of the objective function using a measure of independence between the reduced noise subtraction image and the mask image.

9. An apparatus for intelligent digital subtraction comprising:
   means for obtaining a mask image having highlighted vessels;
   means for obtaining a guide wire image of a guide wire inserted into a vessel;
   means for generating a direct subtraction image from the guide wire image and the mask image; and
   means for generating a reduced noise direct subtraction image based on mutual information between the direct subtraction image and the guide wire image and mutual image information between the mask image and the direct subtraction image.

10. The apparatus of claim 9, wherein said means for obtaining a mask image comprises:
    means for acquiring a sequence of x-ray images with a contrast media injected into the vessels; and means for generating the mask image by determining the minimum intensity of each pixel in the sequence of x-ray images.

11. The apparatus of claim 9, wherein said means for obtaining a guide wire image comprises:
means for receiving an x-ray image of a guide wire inserted into the vessel without contrast media in the vessels.

12. The apparatus of claim 9, wherein said means for generating a direct subtraction image comprises:
means for normalizing the guide wire image and the mask image; and
means for subtracting the normalized mask image from the normalized guide wire image.

13. The apparatus of claim 12, wherein said means for normalizing the guide wire image and the mask image comprises:
means for normalizing the guide wire image and the mask image with a logarithm function.

14. The apparatus of claim 9, wherein said means for generating a reduced noise direct subtraction image comprises:
means for reducing noise in the direct subtraction image by preserving image information in the direct subtraction image that is mutual to the mask image or the guide wire image, and removing image information in the direct subtraction image that is independent of the mask image and the guide wire image.

15. The apparatus of claim 9, wherein said means for generating a reduced noise direct subtraction image comprises:
means for solving an objective function having a first mutual information term for mutual image information between the guide wire image and the reduced noise direct subtraction image a second mutual information term for mutual image information between the mask image and the reduced noise direct subtraction image.

16. The apparatus of claim 15, wherein means for generating a reduced noise direct subtraction image comprises:
approximating the first mutual information term of the objective function using a measure of independence between the reduced noise subtraction image and the guide wire image, and approximating the second mutual information term of the objective function using a measure of independence between the reduced noise subtraction image and the mask image.

17. A computer readable medium encoded with computer executable instructions for intelligent digital subtraction, the computer executable instructions defining steps comprising:
obtaining a mask image having highlighted vessels;
obtaining a guide wire image of a guide wire inserted into a vessel;
generating a direct subtraction image from the guide wire image and the mask image; and
generating a reduced noise direct subtraction image based on mutual information between the direct subtraction image and the guide wire image and mutual image information between the mask image and the direct subtraction image.

18. The computer readable medium of claim 17, wherein the computer executable instructions defining the step of obtaining a mask image comprise computer executable instructions defining the steps of:
acquiring a sequence of x-ray images with a contrast media injected into the vessels; and
generating the mask image by determining the minimum intensity of each pixel in the sequence of x-ray images.

19. The computer readable medium of claim 17, wherein the computer executable instructions defining the step of obtaining a guide wire image comprise computer executable instructions defining the step of:
receiving an x-ray image of a guide wire inserted into the vessel without contrast media in the vessels.

20. The computer readable medium of claim 17, wherein the computer executable instructions defining the step of generating a direct subtraction image comprise computer executable instructions defining the steps of:
normalizing the guide wire image and the mask image; and
subtracting the normalized mask image from the normalized guide wire image.

21. The computer readable medium of claim 20, wherein the computer executable instructions defining the step of normalizing the guide wire image and the mask image comprise computer executable instructions defining the step of:
normalizing the guide wire image and the mask image with a logarithm function.

22. The computer readable medium of claim 17, wherein the computer executable instructions defining the step of generating a reduced noise direct subtraction image comprise computer executable instructions defining the step of:
reducing noise in the direct subtraction image by preserving image information in the direct subtraction image that is mutual to the mask image or the guide wire image, and removing image information in the direct subtraction image that is independent of the mask image and the guide wire image.

23. The computer readable medium of claim 17, wherein the computer executable instructions defining the step of generating a reduced noise direct subtraction image comprise computer executable instructions defining the step of:
solving an objective function having a first mutual information term for mutual image information between the guide wire image and the reduced noise direct subtraction image and a second mutual information term for mutual image information between the mask image and the reduced noise direct subtraction image.

24. The computer readable medium of claim 23, wherein the computer executable instructions defining the step of generating a reduced noise direct subtraction image comprise computer executable instructions defining the step of:
approximating the first mutual information term of the objective function using a measure of independence between the reduced noise subtraction image and the guide wire image, and approximating the second mutual information term of the objective function using a measure of independence between the reduced noise subtraction image and the mask image.

* * * * *